US011406694B2

(12) United States Patent
Good et al.

(10) Patent No.: US 11,406,694 B2
(45) Date of Patent: Aug. 9, 2022

(54) VACCINE COMPRISING DRUG AND PARASITE ADMINISTRATION

(71) Applicant: GRIFFITH UNIVERSITY, Nathan (AU)

(72) Inventors: Michael Good, Nathan (AU); Danielle Stanisic, Nathan (AU); Leanne Low, Nathan (AU)

(73) Assignee: Griffith University, Queensland (AU)

( * ) Notice: Subject to any disclaimer, the term of this patent is extended or adjusted under 35 U.S.C. 154(b) by 0 days.

(21) Appl. No.: 16/333,675

(22) PCT Filed: Oct. 24, 2016

(86) PCT No.: PCT/AU2016/050998
§ 371 (c)(1),
(2) Date: Mar. 15, 2019

(87) PCT Pub. No.: WO2018/049459
PCT Pub. Date: Mar. 22, 2018

(65) Prior Publication Data
US 2019/0224293 A1    Jul. 25, 2019

(30) Foreign Application Priority Data

Sep. 16, 2016 (AU) .............................. 2016903741

(51) Int. Cl.
| | | |
|---|---|---|
| *A61K 39/002* | (2006.01) | |
| *A61K 39/018* | (2006.01) | |
| *A61P 33/06* | (2006.01) | |
| *A61K 31/65* | (2006.01) | |
| *A61K 39/015* | (2006.01) | |
| *A61P 33/02* | (2006.01) | |
| *A01K 67/027* | (2006.01) | |
| *A61K 31/435* | (2006.01) | |
| *A61K 31/7056* | (2006.01) | |
| *A61K 39/00* | (2006.01) | |

(52) U.S. Cl.
CPC ........ *A61K 39/018* (2013.01); *A01K 67/0273* (2013.01); *A61K 31/435* (2013.01); *A61K 31/65* (2013.01); *A61K 31/7056* (2013.01); *A61K 39/002* (2013.01); *A61K 39/015* (2013.01); *A61P 33/02* (2018.01); *A61P 33/06* (2018.01); *A01K 2207/12* (2013.01); *A01K 2207/20* (2013.01); *A01K 2227/105* (2013.01); *A01K 2267/0337* (2013.01); *A61K 2039/521* (2013.01); *A61K 2039/70* (2013.01); *Y02A 50/30* (2018.01)

(58) Field of Classification Search
CPC .... A61K 39/00; A61K 39/002; A61K 39/015; A61K 49/00
USPC .................... 424/9.1, 9.2, 93.1, 265.1, 268.1
See application file for complete search history.

(56) References Cited

FOREIGN PATENT DOCUMENTS

| WO | WO2012/135064 | * 10/2012 | ........... A61K 31/215 |
|---|---|---|---|
| WO | WO 2012/135064 | 10/2012 | |
| WO | WO 2012/162731 | 12/2012 | |
| WO | WO 2015/013739 | 2/2015 | |
| WO | WO 2015/070204 | 5/2015 | |

OTHER PUBLICATIONS

Wittlin, S., et al. Antimicobial Agents and Chemotherapy, 56(2):703-707, 2012.*
Neerja, J., et al. Experimental Parasitology, 107:120-124, 2004.*
1986, Taylor et al. The Veterinary Record, 118:98-102.*
Taylor et al. (7the Veterinary Record, 118:98-102, 1986).*
Wykes et al (Eur. J. Immunol 2009. 39: 1991-2058).*
Büyükbaba Boral et al., "Investigation of combined effectiveness of spiramycin and beta-glucan in mice models of acute toxoplasmosis and determination of IL-10, IL-12 and TNF-alpha levels," *Mikrobiyol Bul.*, 46(3):446-55, 2012. (English Abstract of Turkish publication).
Neerja et al., "Plasmodium yoelii: activity of azithromycin in combination with pyrimethamine or sulfadoxine against blood and sporozoite induced infections in Swiss mice," *Exp Parasitol.*, 107(3-4): 120-4, 2004.
PCT International Search Report and Written Opinion issued in International Application No. PCT/AU2016/050998, dated May 25, 2017.
Taylor et al., "Inhibition of Babesia divergens in cattle by oxytetracycline," *Vet Rec.*, 118(4):98-102, 1986.
Wittlin et al., "In vitro and in vivo activity of solithromycin (CEM-101) against *Plasmodium* species," *Antimicrob Agents Chemother.*, 56(2):703-7, 2011.

* cited by examiner

*Primary Examiner* — Jennifer E Graser
(74) *Attorney, Agent, or Firm* — ParkerHighlander PLLC

(57) ABSTRACT

Apicomplexan parasites or red blood cells infected with apicomplexan parasites are administered to an animal in combination with a delayed death agent that initially allows parasite replication but subsequently kills the apicomplexan parasites. This allows the elicitation of an immune response by the animal while preventing the parasites producing a serious infection of the animal. The apicomplexan parasites may be malaria or babesia parasites. The delayed death agent may be a tetracycline class antibiotic, a macrolide antibiotic or a lincosamide antibiotic.

20 Claims, 9 Drawing Sheets
Specification includes a Sequence Listing.

VACCINE COMPRISING DRUG AND PARASITE ADMINISTRATION

This application is a national phase application under 35 U.S.C. § 371 of International Application No. PCT/AU2016/050998, filed Oct. 24, 2016, which claims the benefit of Australian Patent Application No. 2016903741, filed Sep. 16, 2016, the entirety of each of which is incorporated herein by reference.

Pursuant to 37 C.F.R. 1.821(c), a sequence listing is submitted herewith as an ASCII compliant text file named "SPFEP0002US_ST25.txt", created on Mar. 14, 2019 and having a size of ~2 kilobytes. The content of the aforementioned file is hereby incorporated by reference in its entirety.

TECHNICAL FIELD

THIS INVENTION relates to malaria and other apicomplexan parasites such as Babesia. More particularly, this invention relates a vaccine against blood-stage malaria and other apicomplexans.

BACKGROUND

An effective malaria vaccine will represent a cost-effective and sustainable addition to the currently available malaria control interventions. Malaria vaccines have attempted to target the different stages of malaria infection, typically referred to as the "sporozoite stage", the "liver stage" and "blood-stage". The liver stage occurs when sporozoites infect host hepatocytes, multiplying asexually and asymptomatically for a period of 8-30 days. Once in the liver, these organisms differentiate to yield thousands of merozoites which, following rupture of their host cells, escape into the blood and infect red blood cells, thus beginning the erythrocytic or "blood-stage" of the life cycle. Within the red blood cells, the parasites multiply further, again asexually, periodically breaking out of their hosts to invade fresh red blood cells. Several such amplification cycles occur. Thus, classical descriptions of waves of fever arise from simultaneous waves of merozoites escaping and infecting red blood cells.

Anti-asexual blood-stage vaccines have been aimed at reducing parasite growth and multiplication in the blood and, hence, the occurrence or severity of symptoms. Such vaccines should reduce morbidity and mortality due to malaria in the most susceptible groups (e.g. young children and pregnant women) living in areas where malaria is endemic.

One approach has been to trial recombinant subunit vaccines against blood-stage malaria, but to date none of the subunit blood-stage vaccine candidates have progressed beyond Phase III trials.

An alternative approach has been to use whole blood-stage parasites (e.g. merozoites). Whole blood-stage parasites were first administered to monkeys in 1948 when Freund attempted to develop a whole parasite vaccine. Over the following 30 years there were in excess of 12 separate studies in monkeys (summarized in McCarthy and Good, 2010) until malaria antigens were first cloned in 1983, which ushered in the subunit paradigm era. The whole parasite strategy was abandoned for blood-stage vaccine development because very large numbers of parasites were thought to be required ($5 \times 10^7$-$10^{10}$), making it impossible to prepare such a vaccine at scale in human blood. The only adjuvant shown to be useful was the human-incompatible complete Freund's adjuvant.

More recently, a "low-dose whole parasite" approach has been attempted which may be characterized as follows: (i) it aims to induce a cellular (T cell) immune response, as opposed to an antibody response; (ii) very low doses of parasites are not only sufficient but essential to keep doses low; and (iii) heterologous immunity is induced because presumably the target antigenic determinants of T cells are highly conserved between *Plasmodium* strains and species (Pinzon-Charry et al, 2010), thereby obviating one of the major impediments of sub-unit vaccines that aim to induce antibodies that target polymorphic merozoite or infected red cell surface proteins. Furthermore, very low doses of parasites overcome the logistic impediment of finding sufficient blood to prepare a vaccine at scale or the need to find a way to grow the parasites in axenic culture. The two critical factors of parasite dose and cellular immune response are in fact closely related. In order to induce a strong cellular immune response, it is important to use only a very low dose of parasites (Elliott et al, 2005).

Three studies are reported in which humans or mice have been immunized with ultra-low doses of whole parasites—two in which vaccinees received an ultra-low dose of live infected red cells (with infection terminated by malarone 48 hours later and before parasites were visible in the blood by microscopy; Elliott et al, 2005; Pombo et al, 2002), and the other in which mice were immunized with 100-1000 killed infected red cells mixed with CpG and Alum for the primary immunization (Pinzon-Charry et al, 2010). In both humans and mice the immune responses were characterized by a strong in vitro proliferative response to parasites of $CD4^+$+/− $CD8^+$ T cells, secretion of γ-interferon and induction of nitric oxide synthase in peripheral blood mononuclear cells. Parasite-specific antibodies were either not induced, or induced at very low levels. Memory T cells (both 'central' and 'effector') were induced. It has been proposed that induced memory T cells will have specificity for internal antigens of the parasite and that these will be highly conserved as they are not under immune selective pressure from B cells and antibody.

It will be appreciated that because the dose of administered parasites was low, the volunteers in Pombo et al., 2012, supra never developed any symptoms of malaria by the time of treatment. However, this strategy was unsuitable as a vaccine because if the vaccinated subjects did not return, or returned too late for subsequent malarone (or other antimalarial drug treatment), the parasite infection would develop beyond 8 days and become very serious.

SUMMARY

Surprisingly, co-administration of blood-stage malaria parasites and a delayed death agent provide effective immunization against malaria. The delayed death agent poisons the apicoplasts present in apicomplexan parasites such as malaria and as such allows limited replication of the blood-stage parasites before killing the parasites, thereby allowing the immune system to mount a response to the parasites while preventing a serious infection to develop.

The invention is therefore broadly directed to an immunogenic composition for co-administering blood-stage apicomplexan parasites or parasitized red blood cells, together with a delayed death agent, preferably in the absence of adjuvant.

In one aspect, the invention provides a method of producing an immunogenic composition including the step of combining apicomplexan parasites or red blood cells infected with said parasites with a delayed death agent, to thereby produce said immunogenic composition.

Suitably, the method excludes the step of including or administering an adjuvant.

In another aspect, the invention provides an immunogenic composition comprising apicomplexan parasites or red blood cells infected with said apicomplexan parasites in combination with a delayed death agent; and an acceptable carrier, diluent or excipient.

Suitably, the immunogenic composition does not include an adjuvant.

In yet another aspect, the invention provides apicomplexan parasites or red blood cells infected with said apicomplexan parasites and a delayed death agent for use in for eliciting an immune response to an apicomplexan parasite, or for preventing or treating or immunizing against an apicomplexan parasite infection.

In still yet another aspect, the invention provides apicomplexan parasites or red blood cells infected with said apicomplexan parasites and a delayed death agent in the manufacture of a medicament for eliciting an immune response to an apicomplexan parasite, or for preventing or treating or immunizing against an apicomplexan parasite infection in an animal.

Suitably, the medicament does not include an adjuvant.

In a further aspect, the invention provides a method of eliciting an immune response to an apicomplexan parasite, said method including the step of co-administering blood-stage apicomplexan parasites or red blood cells infected with said apicomplexan parasites and a delayed death agent to an animal to thereby elicit an immune response to an apicomplexan parasite in said animal.

In another further aspect, the invention provides a method of treating or preventing an apicomplexan parasite infection, said method including the step of co-administering blood-stage apicomplexan parasites or red blood cells infected with said apicomplexan parasites and a delayed death agent to an animal to thereby prevent or inhibit an apicomplexan parasitic infection or treat an existing apicomplexan parasitic infection in said animal.

In yet another further aspect, the invention provides a method of immunizing against an apicomplexan parasite infection, said method including the step of co-administering blood-stage apicomplexan parasites or red blood cells infected with said apicomplexan parasites and a delayed death agent to an animal to thereby immunize the animal against the apicomplexan parasite infection.

Suitably, the method does not include administration of an adjuvant.

An aspect of the invention provides a method of producing an animal for vaccine testing, said method including the step of co-administering apicomplexan parasites or red blood cells infected with said apicomplexan parasites and a delayed death agent to the animal to thereby produce a controlled parasite infection in said animal.

Suitably, the method does not include administration of an adjuvant.

A related aspect of the invention provides a method of testing a vaccine in animal, said method including the step of administering a candidate apicomplexan parasite vaccine to an animal after co-administering apicomplexan parasites or red blood cells infected with said apicomplexan parasites and a delayed death agent to the animal.

Suitably, the method includes the step of determining the efficacy of the vaccine after administration to the animal.

Suitably, the method does not include administration of an adjuvant.

In some embodiments of the aforementioned aspects, the apicomplexan parasites or infected red blood cells are a "low dose" of apicomplexan parasites.

Suitably, the apicomplexan parasites include, or are, merozoites, schizonts, rings or trophozoites, although without limitation thereto.

In one embodiment, the apicomplexan parasite is a malaria parasite.

In another embodiment, the apicomplexan parasite is a Babesia parasite.

Preferably, the animal of the aforementioned aspects is a mammal such as a human or bovine.

Throughout this specification, unless the context requires otherwise, the words "comprise", "comprises" and "comprising" will be understood to imply the inclusion of a stated integer or group of integers but not the exclusion of any other integer or group of integers.

DETAILED DESCRIPTION

Figure 1:
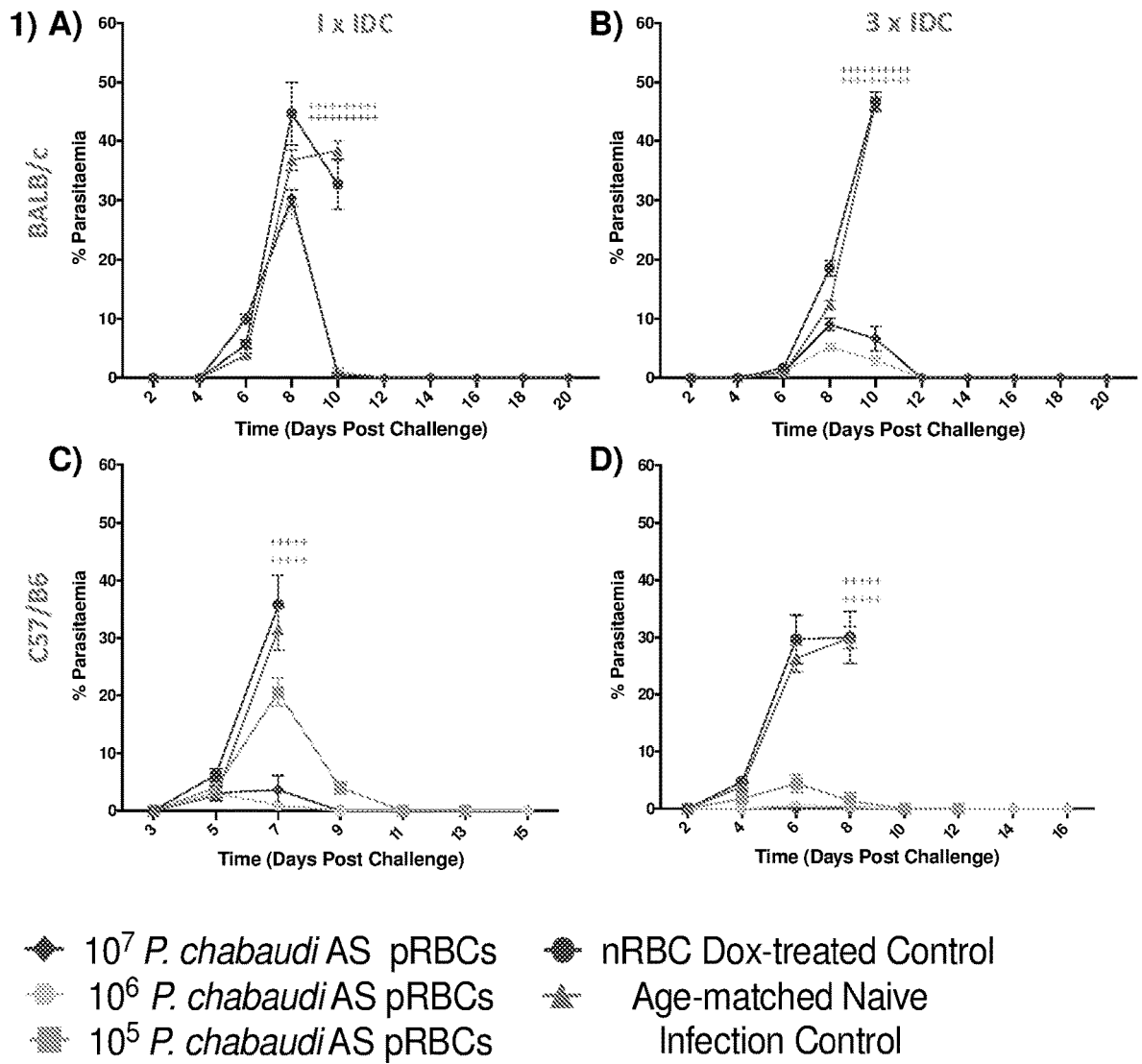
FIG. 1: Parasitaemia of BALB/c mice (n=10/group; top panel) receiving A) 1×Infection and Drug Cure (IDC) and B) 3×IDC with *P. chabaudi* AS, and C57/B6 mice (n=5/group; bottom panel) receiving C) 1×IDC and D) 3×IDC with *P. chabaudi* AS followed by homologous challenge with $10^5$ *P. chabaudi* AS. Immunised groups received $10^5$, $10^6$, or $10^7$ *P. chabaudi* AS parasitised red blood cells (pRBCs) under doxycycline treatment, while aged-matched groups received $10^7$ normal red blood cells (nRBCs) under doxycycline treatment. Mice were exposed to a homologous challenge 4 weeks after the last IDC with $10^5$ *P. chaubaudi* AS and aged-matched nave mice acted as a naïve infection control. + indicated mice that were culled based on clinical scores.

The present invention is predicated at least partly on the discovery that co-administration of blood-stage malaria parasites (e.g merozoites, schizonts, rings or trophozoites, although without limitation thereto) or red blood cells infected with same, together with a delayed death agent such as doxycycline, effectively immunize against subsequent malaria infection in the absence of adjuvant. The delayed death agent initially allows a limited number of cycles of replication of the administered blood-stage malaria parasites before killing them, giving the blood-stage malaria parasites more exposure to the host immune system and thereby enabling the elicitation of a host immune response that may be protective. It is proposed that this approach should be applicable to other apicomplexan parasites, as the delayed death agent may target the apicomplex organelle to thereby exert its delayed death effect.

Accordingly, in one aspect, the invention provides a method of producing an immunogenic composition including the step of combining isolated or purified apicomplexan parasites or red blood cells infected with said apicomplexan parasites together with a delayed death agent, to thereby produce said immunogenic composition.

In another aspect, the invention provides an immunogenic composition for preventing or treating an apicomplexan parasite infection, said immunogenic composition comprising isolated or purified apicomplexan parasites or red blood cells infected with said apicomplexan parasites in combination with a delayed death agent.

In yet another aspect, the invention provides isolated or purified apicomplexan parasites or red blood cells infected with said apicomplexan parasites and a delayed death agent for use in combination for eliciting an immune response to an apicomplexan parasite or for preventing or treating or immunizing against an apicomplexan parasite infection.

In a further aspect, the invention provides a method of eliciting an immune response to an apicomplexan parasite, said method including the step of co-administering blood-stage apicomplexan parasites or red blood cells infected with said apicomplexan parasites and a delayed death agent to an animal to thereby elicit an immune response to an apicomplexan parasite in said animal.

In another further aspect, the invention provides a method of treating or preventing an apicomplexan parasite infection, said method including the step of co-administering blood-stage apicomplexan parasites or red blood cells infected with said apicomplexan parasites and a delayed death agent to an animal to thereby prevent or inhibit an apicomplexan parasitic infection or treat an existing apicomplexan parasitic infection in said animal.

In yet another further aspect, the invention provides a method of immunizing against an apicomplexan parasite infection, said method including the step of co-administering blood-stage apicomplexan parasites or red blood cells infected with said apicomplexan parasites and a delayed death agent to an animal to thereby immunize the animal against the apicomplexan parasite infection.

The "delayed death agent" may be any molecule or compound that is cytotoxic or otherwise capable of killing apicomplexan parasites, preferably blood-stage apicomplexan parasites, while allowing no more than one, two, three, four, five or more cycles of replication by the apicomplexan parasites following co-administration to an animal before killing the apicomplexan parasites. Suitably, the delayed death agent targets the apicomplex organelle of the parasite to thereby exert its delayed death effect. The delayed death agent may be an antibiotic. In one embodiment, the delayed death agent is a tetracycline class antibiotic. In particular embodiments the delayed death agent may be doxycycline, minocycline, sancycline or other tetracycline class antibiotic, such as described in Draper et al., 2013. In other embodiments, delayed-death agents may include macrolide antibiotics such as azithromycin and lincosamide antibiotics such as clindamycin. Reference herein to delayed death agents also includes free acid or base forms, isomers, racemates, enantiomers, polymorphs, salts, hydrates and other forms of derivatives of such agents. Non-limiting examples include hydrochlorides, chlorides, phosphates, sulphates, tosylates, mesylates, oxalates, succinates, hydrates inclusive of hemihydrates, monohydrates, and dihydrates, carrageenates, calcium, magnesium, sodium and potassium salts, although without limitation thereto.

Suitable dosages of delayed death agent for use in humans may be about 10-500 mg, preferably about 50-250 mg, more preferably about 70, 80, 90, 100, 110, 120 or 130 mg, or any dosage range therebetween It will also be appreciated that that delayed death agent need not kill all or even a substantial portion of the administered blood-stage malaria parasites. Suitably, the delayed death agent kills a portion of the administered blood-stage malaria parasites, or their progeny, sufficient to prevent the administered blood-stage malaria parasites, or their progeny, establishing an infection in the animal host.

In some embodiments, these dosages may be administered once, twice or more daily.

As hereinbefore described, the delayed death agent may be co-administered with apicomplexan parasites or pRBC.

By "co-administered" and "co-administration" in this context is meant that the apicomplexan parasites and the delayed death agent are, at least initially, administered to an animal in a temporal window whereby the delayed death agent can allow no more than one, two, three, four or five cycles of replication by the administered apicomplexan parasites before killing the apicomplexan parasites. This may include simultaneous administration together in the same composition, simultaneous administration separately (e.g in separate or discrete compositions), or sequential administration (e.g in separate or discrete compositions), separated by a limited time period, such as less than 48 hrs, less than 36 hrs, less than 30 hrs, less than 24 hrs, less than 12 hours, less than 8 hours, less than 4 hours, less than 2 hours, less than 1 hour or no more than about 5, 10, 15, 20, 25, 30, 35, 40 or 45 minutes. Suitably, for separate administration the apicomplexan parasites are administered first followed by administration of the delayed death agent. However, the delayed death agent could be administered before the apicomplexan parasites are administered. The same temporal window referred to above could be used in this situation. Co-administration may also include one or a plurality of further doses of the delayed death agent and/or one or a plurality of further administrations of the apicomplexan parasites. Further doses may be delivered together in the same composition or in separate or discrete compositions as hereinbefore described. Further doses of the delayed death agent and/or further administration of the apicomplexan parasites may continue one or twice daily or periodically for up to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40 or more days.

As used herein "apicomplexa" and "apicomplexan" refer to a phylum of parasitic protists that typically possess an apicomplex, an organelle that comprises a apicoplast-type plastid and an apical complex structure. The organelle is an adaptation that the apicomplexan parasite applies in penetration of a host cell. In certain embodiments, the apicomplexan parasite is a malaria parasite or a Babesia parasite. Non-limiting examples of other apicomplexan parasites include *Cryptosporum*, *Cryptosporidium* and *Toxoplasma* parasites.

Suitably, the apicomplexan parasites co-administered to the animal with the delayed death agent are "living" or "live" parasites capable of replication. Suitably, the parasites have not been attenuated, such as either genetically or chemically. Suitably, apicomplexan parasites are blood-stage parasites. Typically, blood stage apicomplexan parasites are, or include, merozoites, schizonts, rings or trophozoites, although without limitation thereto. For example, the blood-stage apicomplexan parasites may be isolated or purified blood-stage apicomplexan parasites such as schizonts, rings and/or trophozoites or may be mixtures of one or more of these blood-stage types. Alternatively, the blood-stage malaria parasites may be in the form of parasitized red blood cells (pRBC). Suitably, the pRBC comprise living or live apicomplexan parasites capable of replication and have not been attenuated either genetically or chemically.

In this context, by "isolated" is meant material (e.g. apicomplexan parasites or pRBC) that has been removed from its natural state or otherwise been subjected to human manipulation. Isolated material may be substantially or essentially free from components that normally accompany it in its natural state, or may be manipulated so as to be in an artificial state together with components that normally accompany it in its natural state. Isolated material (e.g. blood-stage apicomplexan parasites such as merozoites, schizonts, trophozoites or rings or pRBC) may be in purified, partially purified or an otherwise enriched form.

The pRBC may be obtained from blood of a apicomplexan parasite-infected animal. Alternatively, to produce pRBC in vitro, non-infected red blood cells may be obtained from an animal and then infected in vitro with blood-stage apicomplexan parasites.

A preferred feature of the present invention is that the blood-stage apicomplexan parasites, such as merozoites, schizonts, trophozoites or rings, or pRBC are administered to the animal at a low dose.

The blood-stage apicomplexan parasites (such as merozoites, schizonts, rings or trophozoites, although without limitation thereto) are suitably administered at a dose capable of inducing a T cell response when administered to an animal. Preferably, the immune response is characterised by inducing a T cell response and preferably not inducing B cells to produce detectable levels, or only low levels, of antibodies. A low level of antibody production preferably refers to a level that would not be sufficient to protect an animal against the apicomplexan parasite.

The apicomplexan parasites may be administered in an enriched or purified form, or as parasite-infected red blood cells (pRBC). The pRBC may be administered as intact cells or as a lysate. Preferably, the pRBC are in intact form.

A typical dose is no more than $10^{10}$ apicomplexan parasites or pRBC such as including $5 \times 10^9$, $5 \times 10^8$, $10^8$, $5 \times 10^7$, $10^7$, $5 \times 10^6$, $10^6$, $5 \times 10^5$, $10^5$, $5 \times 10^4$, $10^4$, $5 \times 10^3$, $10^3$, $5 \times 10^2$, $10^2$, $5 \times 10^1$ or $10^1$ apicomplexan parasites or pRBC. Particular dose ranges include $10^1$-$10^9$, $10^1$-$10^8$, $10^1$-$10^7$, $10^1$-$10^6$, $10^1$-$10^5$, $10^1$-$10^4$, $10^1$-$10^3$, $10^1$-$10^2$, $10^2$-$10^8$, $10^2$-$10^7$, $10^2$-$10^6$, $10^2$-$10^5$, $10^2$-$10^4$, $10^2$-$10^3$, $10^3$-$10^8$, $10^3$-$10^7 10^3$- $10^6$, $10^3$-$10^5$, $10^3$-$10^4$, $10^4$-$10^8$, $10^4$-$10^7 10^4$-$10^6$, $10^4$-$10^5$, $10^5$-$10^8$, $10^5$-$10^7$, $10^5$-$10^6$, $10^6$- $10^7$, $10^6$-$10^8$ $10^7$-$10^8$ or $10^8$-$10^9$ apicomplexan parasites or pRBC per dose.

In some embodiments, a "low dose" of apicomplexan parasites or pRBC are administered. By this is meant an administered dose wherein the resultant parasite density is sufficiently low that the parasite cannot be detected on a blood smear. A low dose may result in a sub-patent infection. In some embodiments, a low dose refers to no more than $10^1$-$10^7$ apicomplexan parasites or pRBC.

In one embodiment, the apicomplexan parasites are malaria parasites. Preferably, the malaria parasites are blood-stage malaria parasites.

As used herein, "malaria" includes all forms of the disease caused by protozoan protists of the genus *Plasmodium*.

The genus "*Plasmodium*" includes the species *Plasmodium falciparum*, *Plasmodium vivax*, *Plasmodium malariae*, *Plasmodium ovale*, *Plasmodium knowlesi*, *Plasmodium berghei*, *Plasmodium yoelii*, *Plasmodium chabaudi* and *Plasmodium vinckei*. In embodiments relevant to malaria in humans, the causative *Plasmodium* species are typically *Plasmodium falciparum* and *Plasmodium vivax*. Suitably, for treatment of humans the immunogenic composition and method of prophylactic or therapeutic treatment of malaria comprises merozoites of one or more strains or isolates of *Plasmodium falciparum* and/or *Plasmodium vivax*.

One preferred, unexpected advantage of the present invention is that the blood-stage malaria parasites of a particular *Plasmodium* isolate, strain or species will, upon administration to an animal, immunize against infection by heterologous *Plasmodium* isolates, strains and/or species. By "heterologous" pathogens means related pathogens that may be different strains or variants of a same or related species. An example of different strains of a same species is *P. c. chabaudi* AS and *P. c. chabaudi* CB. Heterologous may also refer to related species for example, *P. falciparum* and *P. vivax*.

In one embodiment, the apicomplexan parasites are Babesia parasites. Preferably, the babesia parasites are blood-stage Babesia parasites.

Babesiosis is a group of diseases and conditions of mammals caused by, or otherwise associated, apicomplexan protists of the genus Babesia. Babesiosis may occur in mammals such as cattle, buffalo, pigs, deer, dogs, sheep, donkeys, horses and humans, although without limitation thereto. Babesiosis is typically associated with severe haemolytic anaemia and a positive erythrocyte-in-saline-agglutination test indicating an immune-mediated component to haemolysis. Common sequelae include haemoglobinuria "red-water", disseminated intravascular coagulation and "cerebral babesiosis" caused by sludging of erythrocytes in cerebral capillaries. In some cases, babesiosis can prove fatal.

Human babesiosis is uncommon although some cases occur due to tick-borne Babesia *divergens* or Babesia *microti*, a parasite of small mammals. A few human cases have been fatal. Generally, in non-human mammals the main pathogeic species of Babesia include Babesia *bovis*, Babesia *canis*, Babesia bigemena, Babesia *divergens*, Babesia *ovis*, Babesia *ovata*, Babesia *occultans*, Babesia *caballi* and Babesia *motasi*.

The main parasites of bovine mammals are Babesia *bovis*, Babesia *bigemena* and Babesia *divergens*, which cause "tick fever" or "cattle fever", a hemolytic anemia, such that an infected animal will also show pale to yellow mucous membranes due to the failure of the liver to metabolize excess bilirubin.

It will also be appreciated that another preferred advantage of the present invention is that the immunogenic composition and method of treatment obviates the need for an adjuvant, whether separately or as a component of the immunogenic composition. By "adjuvant" is meant an agent which assists, augments or otherwise facilitates the elicitation of an immune response by an immunogen. Non-limiting examples of excluded adjuvants include, Freund's adjuvant, aluminium hydroxide (alum), aluminium phosphate, squalene, IL-12, CpG-oligonucleotide, Montanide ISA720, imiquimod, SBAS2, SBAS4, MF59, MPL, Quil A, QS21 and ISCOMs.

While it is preferred that adjuvant is absent from the immunogenic composition, it will be appreciated that other components such as immunologically acceptable carriers, diluents and/or excipients may be included. Typically, these include solid or liquid fillers, diluents or encapsulating substances that may be safely used in oral or systemic administration. Depending upon the particular route of administration, carriers, diluents and/or excipients may be selected from a group including sugars, starches, cellulose and its derivatives, malt, gelatine, talc, calcium sulfate, vegetable oils, synthetic oils, polyols, alginic acid, isotonic saline, pyrogen-free water, wetting or emulsifying agents, bulking agents, coatings, binders, fillers, disintegrants, lubricants and pH buffering agents (e.g. phosphate buffers) although without limitation thereto. The immunogenic composition and method of prophylactic or therapeutic treatment of malaria may be administered to an animal in any one or more dosage forms that include tablets, dispersions, suspensions, injectable solutions, slow-release formulations, syrups, troches, capsules, suppositories, aerosols, transdermal patches and the like.

In some embodiments, the delayed death agent is administered as a slow-release formulation, controlled release formulation or delayed release formulation. The slow release formulation may provide continuous release of the delayed death agent, preferably at a desired dosage, for up to 3, 4, 5, 6, 7, 8, 9, 10, 11, 12, 13, 14, 15, 16, 17, 18, 19, 20, 21, 22, 23, 24, 25, 26, 27, 28, 29, 30, 32, 33, 34, 35, 36, 37, 38, 39 or 40 or more days after administration to the animal.

A delayed release formulation may release the delayed death agent, preferably at a desired dosage, beginning 1, 2, 3, 4, 5 or 6 days after administration.

Typically, a suitable slow release formulation, controlled release formulation or delayed release formulation comprises a pharmaceutically acceptable polymer that is mixed, combined or otherwise formulated with the delayed death agent to allow the controlled or delayed release of the delayed death agent once administered to an animal. Non-limiting examples of polymers include cellulose derivatives, thermoplastic aliphatic polyesters, poly(ethylene glycol) PEG and poly(N-vinyl pyrrolidone), although without limitation thereto. In some embodiments, the polymer is biodegradable. A non-limiting example of a slow release formulation is a bioabsorbable, flowable polymeric formulation composed of poly(DL lactide) (PLA) dissolved in N-methyl-2-pyrrolidone (NMP), such as the ATRIGEL® Delivery System which can provide controlled release of a delayed death agent for up to 7 days.

Suitably, the immunogenic composition and methods of eliciting an immune response to, immunization against or prevention or treatment of apicomplexan parasitic infections are effective against blood-stage apicomplexan parasites and/or parasitic infections.

Blood-stage infection is a stage where the apicomplexan parasite (e.g. merozoite) enters erythrocytes. In the blood schizont stage, the parasite divides several times to produce new merozoites, which leave the red blood cells and travel within the bloodstream to invade new red blood cells. For the sufferer, blood-stage malaria is typically characterized by successive waves of fever arising from simultaneous waves of merozoites escaping and infecting red blood cells.

The immunogenic composition and methods disclosed herein may elicit an immune response to an apicomplexan parasite, or molecular components thereof, in an animal. By "elicit an immune response" means to induce, stimulate, activate or otherwise facilitate the production and/or activity of one or more elements of an immune response in an animal. These may include cellular elements such as lymphocytes, antigen presenting cells and cells of the innate immune system, cytokines and other molecular mediators of immunity and/or antibodies. Preferably, the immune response is characterized as a $CD4^+$ T cell-mediated response (including solely $CD4^+$ T cell-mediated responses and mixed $CD4^+$ and $CD8^+$ T cell-mediated responses), typically with little or no antibody response. Preferably, the immunogenic composition and/or methods disclosed herein immunize the animal to prevent, inhibit or otherwise protect the animal against a subsequent apicomplexan parasite infection. Preferably, a single dose of the immunogenic composition elicits and immune response and preferably prevents, inhibits or otherwise protects the animal against subsequent apicomplexan parasite infection.

A further aspect of the invention provides a method of producing an animal for vaccine testing, said method including the step of co-administering blood-stage apicomplexan parasites or red blood cells infected with said blood-stage apicomplexan parasites and a delayed death agent to the animal to thereby produce a controlled apicomplexan parasite infection in said animal.

A still further aspect of the invention provides a method of testing an apicomplexan parasite vaccine in animal, said method including the step of administering a candidate vaccine to an animal after co-administering apicomplexan parasites or red blood cells infected with said apicomplexan parasites and a delayed death agent to the animal to produce a controlled infection in said animal.

By "controlled infection" is meant that the apicomplexan parasites are maintained at a desired level that is effectively an avirulent infection that is not harmful to the animal.

Suitably, the method includes the step of determining the efficacy of the vaccine after administration to the animal.

It is proposed that co-administration of apicomplexan parasites and a delayed death agent provides a platform with which to test the efficacy of a candidate vaccine in a volunteer population. The delayed death agent allows the safe administration of living apicomplexan parasites that are of a similar strain, isolate or genetic background to those used for subsequent challenge.

Normally, when challenged with a virulent parasite infection (e.g. a malaria infection), volunteers must be treated as soon as the malaria parasite load exceeds a certain threshold, typically within 1 week of infection. If the vaccine has not started to reduce the parasite burden by that time (and vaccines that induce cellular immunity typically commence to work at about 6 days), or if the vaccine is only partially effective, then that candidate vaccine will be discarded. In such cases, the only way to then test candidate vaccines is in very expensive large scale trials in endemic regions. The present invention allows vaccine efficacy studies to be undertaken in non-endemic regions with smaller sample sizes, thereby dramatically reducing costs As generally used herein "animal" refers to any animal capable of infection by an apicomplexan parasite, particularly mammals inclusive of humans and bovines.

So that preferred embodiments may be described in detail and put into practical effect, reference is made to the following non-limiting Examples.

EXAMPLES

The work described herein relates to giving mice and humans a blood stage malaria infection and daily doses of oral (human) or intraperitoneal (mice) doxycycline as a delayed death agent. This cycle can be repeated and we have given mice 1 or 3 cycles of infection/drug cure (IDC) with doxycycline.

Mice (BALB/c or C57/B6) received varying doses of *Plasmodium* parasite ($10^5$-$10^7$ trophozoite parasitised red blood cells; pRBC), administered via intravenous injection (200 µL). Mice were subsequently started on doxycycline treatment (doxycycline hydrate (Sigma) dissolved in 1× phosphate buffered saline, 50 mg/kg administered in ~100 µL volume via intraperitoneal injection) approximately 1-2 hours post infection. Mice received treatment every day for 7 days. Subsequent infection and drug cures (IDCs) were administered 2 weeks from the day of last treatment (or 3 weeks between infections). Mice were challenged 4 weeks from the day of last treatment of the last round of IDC (or 5 weeks from last infection).

Figure 2:
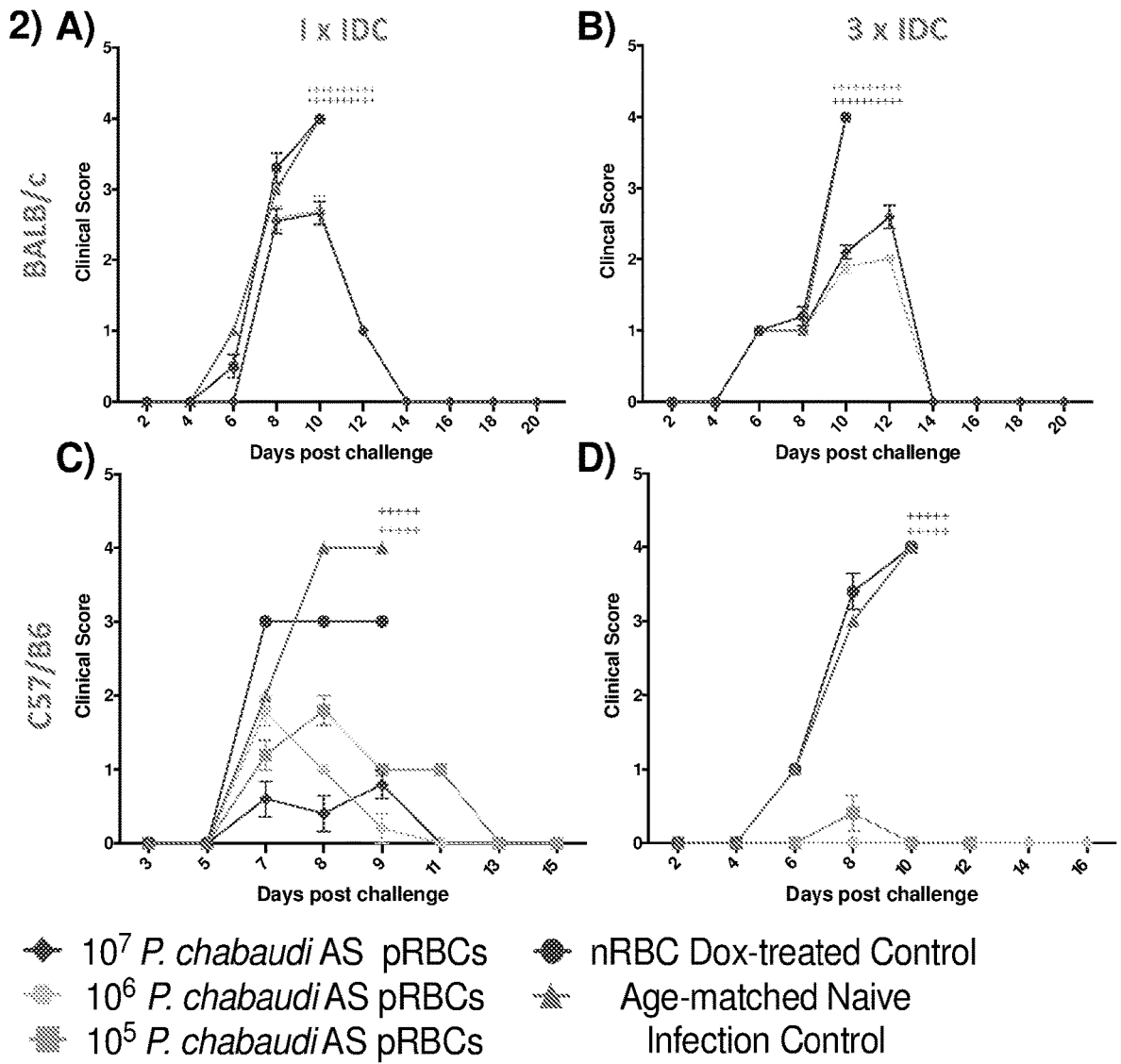
FIG. 2: Clinical scores of BALB/c mice (n=10/group; top panel) receiving A) 1×IDC and B) 3×IDC with *P. chabaudi* AS, and C57/B6 mice (n=5/group; bottom panel) receiving C) 1×IDC and D) 3×IDC with *P. chabaudi* AS followed by homologous challenge with $10^5$ *P. chabaudi* AS. Immunised groups received $10^5$, $10^6$, or $10^7$ *P. chabaudi* AS parasitised red blood cells (pRBCs) under doxycycline treatment, while aged-matched groups received $10^7$ normal red blood cells (nRBCs) under doxycycline treatment. Mice were exposed to a homologous challenge 4 weeks after the last IDC with $10^5$ *P. chaubaudi* AS and aged-matched naïve mice acted as a naïve infection control. + indicated mice that were culled based on clinical scores.

In the mice, the infection takes approximately 4 days to clear and during this time the mice remain well. When the mice are challenged with a live infection (i.e without doxycycline) they demonstrate immunity as shown in FIGS. 1-6. In C57/BL6 mice we observed that one or three cycles of infection/drug cure with *P. chabaudi* leads to strong protection against homologous infection (FIGS. 1 and 2 C-D). However, in BALB/c mice, we observed that three cycles of infection gave better protection than one for *P. chabaudi* (FIGS. 1 and 2 A-B).

Figure 3:
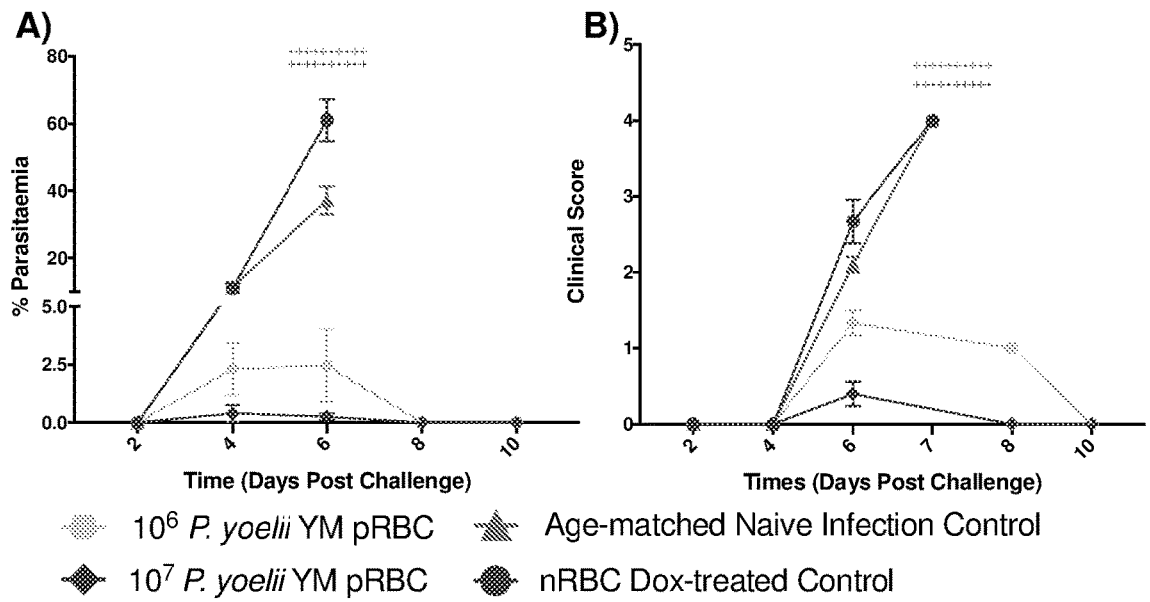
FIG. 3: A) Parasitaemia and B) clinical scores of BALB/c mice (n=10/group) receiving 1×IDC with *P. yoelii* YM, followed by homologous challenge with $10^5$ *P. yoelii* YM. Immunised mice received $10^6$ or $10^7$ *P. yoelii* YM with doxycycline treatment. Controls received $10^7$ nRBCs under doxycycline treatment or were age-matched for challenge. Mice were exposed to a homologous challenge 4 weeks after the last IDC with $10^5$ *P. yoelii* YM and aged-matched naïve mice acted as a naïve infection control. + indicated mice that were culled based on clinical scores.
Figure 4:
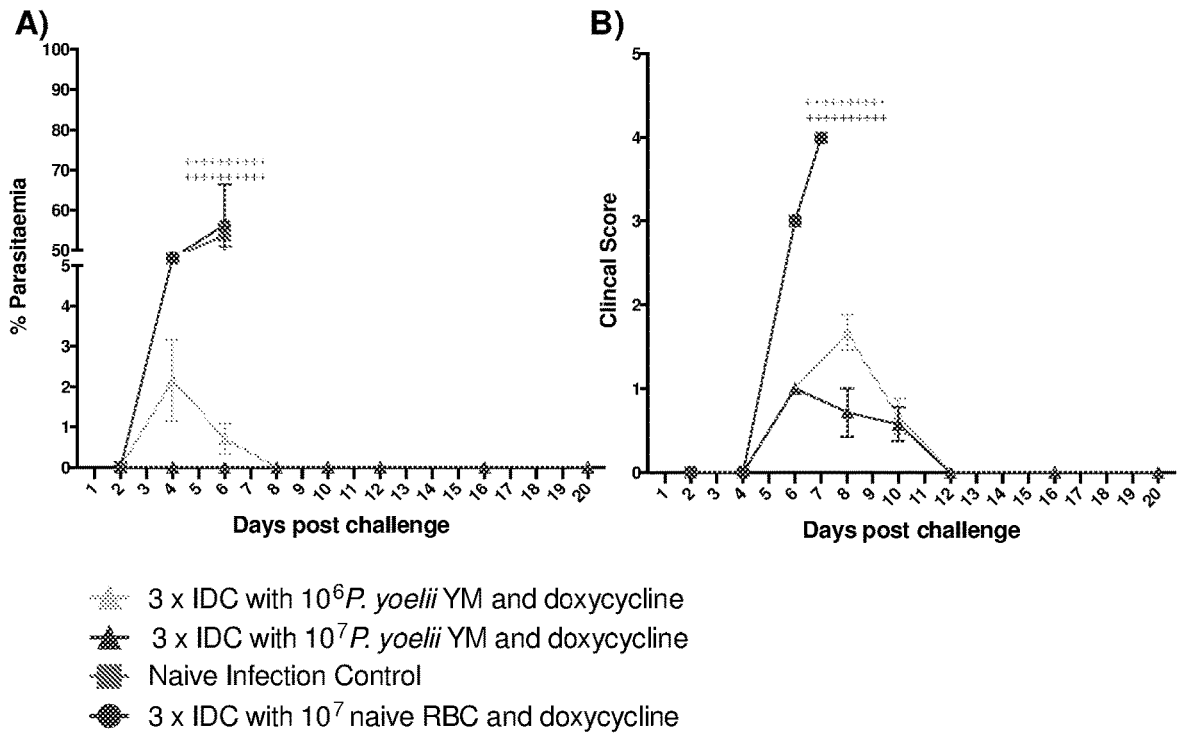
FIG. 4: A) Parasitaemia and B) clinical scores of BALB/c mice (n=10/group) receiving 3×IDC with *P. yoelii* YM, followed by homologous challenge with $10^5$ *P. yoelii* YM. Immunised mice received $10^6$ or $10^7$ *P. yoelii* YM with doxycycline treatment. Controls received $10^7$ nRBCs under doxycycline treatment or were age-matched for challenge. Mice were exposed to a homologous challenge 4 weeks after the last IDC with $10^5$ *P. yoelii* YM and aged-matched naïve mice acted as a naïve infection control. + indicated mice that were culled based on clinical scores.
Figure 5:
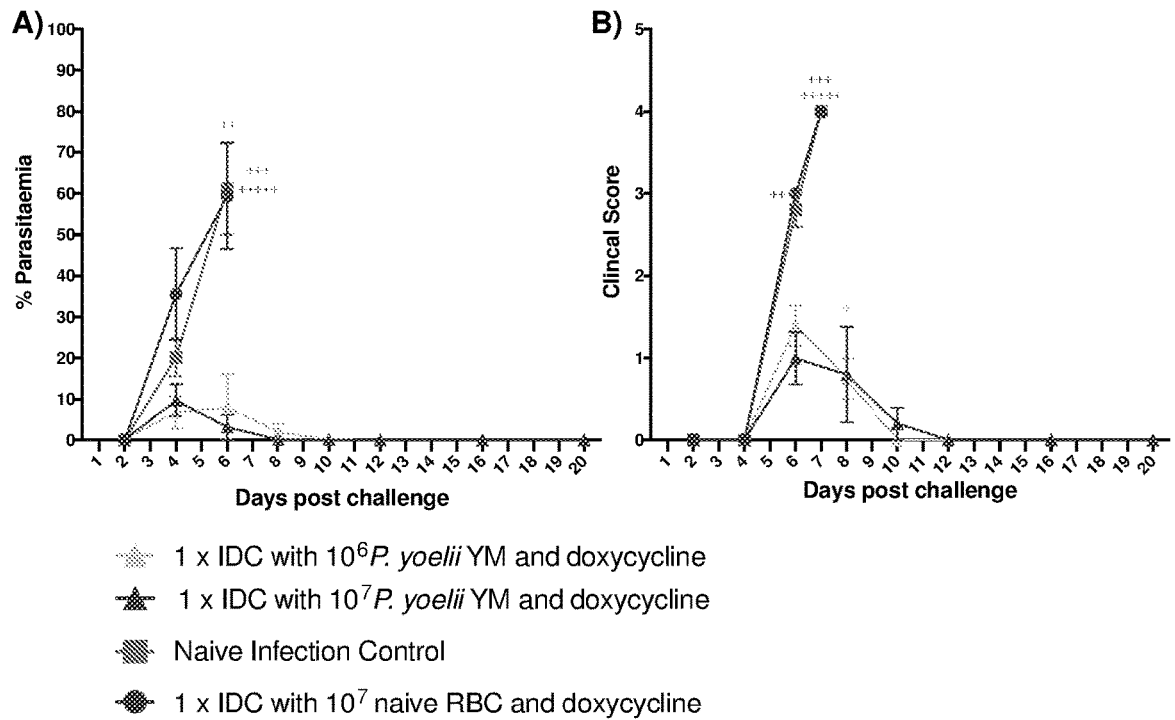
FIG. 5: A) Parasitaemia and B) clinical scores of C57/B6 mice (n=5/group) receiving 1×IDC with *P. yoelii* YM, followed by homologous challenge with $10^5$ *P. yoelii* YM. Immunised mice received $10^6$ or $10^7$ *P. yoelii* YM with doxycycline treatment. Controls received $10^7$ nRBCs under doxycycline treatment or were age-matched for challenge. Mice were exposed to a homologous challenge 4 weeks after the last IDC with $10^5$ *P. yoelii* YM and aged-matched naïve mice acted as a naïve infection control. + indicated mice that were culled based on clinical scores.

Similarly, strong protection was observed when the infection/drug cure was administered with a different species of rodent malaria parasite. In contrast to the IDC model with *P. chabaudi* AS, IDC with *P. yoelii* YM was able to elicit strong protection in BALB/c mice in both one and three cycles of infection/drug cure (FIGS. 3 and 4). In C57/B6 mice, one cycle of infection/drug cure was also able to elicit strong protection during homologous challenge (FIG. 5).

Figure 6:
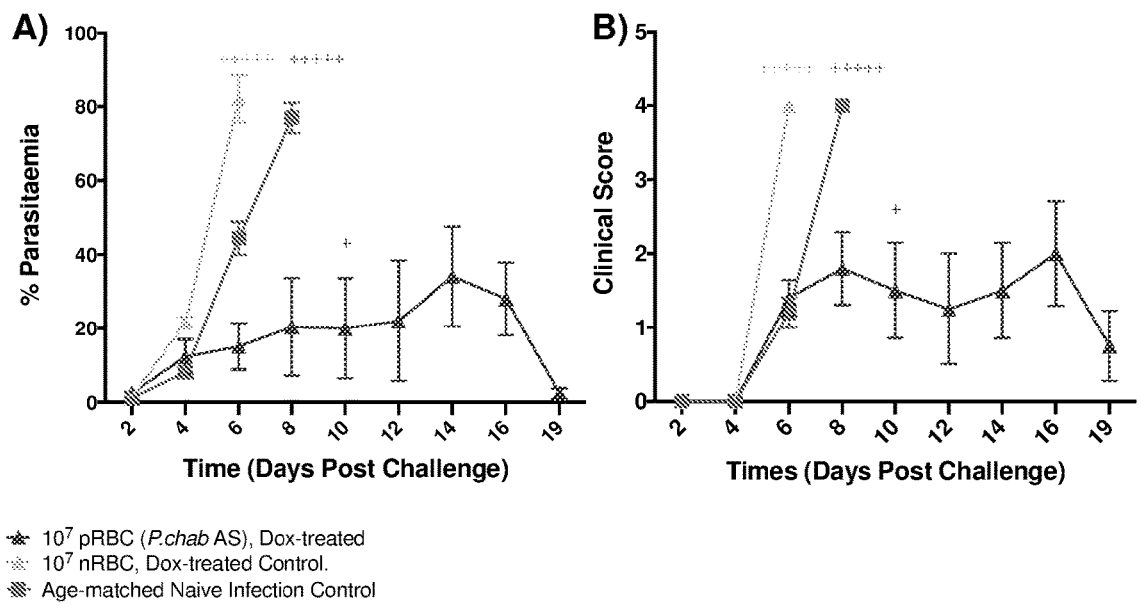
FIG. 6: A) Parasitaemia and B) clinical scores of C57/B6 mice (n=5/group) receiving 1×IDC with $10^7$ *P. chabaudi* AS, followed by heterologous challenge with $10^5$ *P. yoelii* YM. Immunised mice received $10^7$ *P. chabaudi* pRBCs, while control groups received $10^7$ normal RBCs (nRBCs) under doxycycline treatment or were age-matched naïve mice for challenge. + indicated mice that were culled based on clinical scores.

Following vaccination of mice with *P. chabaudi* by IDC, we also observed protection against the heterologous parasite, *P. yoelii* (FIG. 6).

Figure 7:
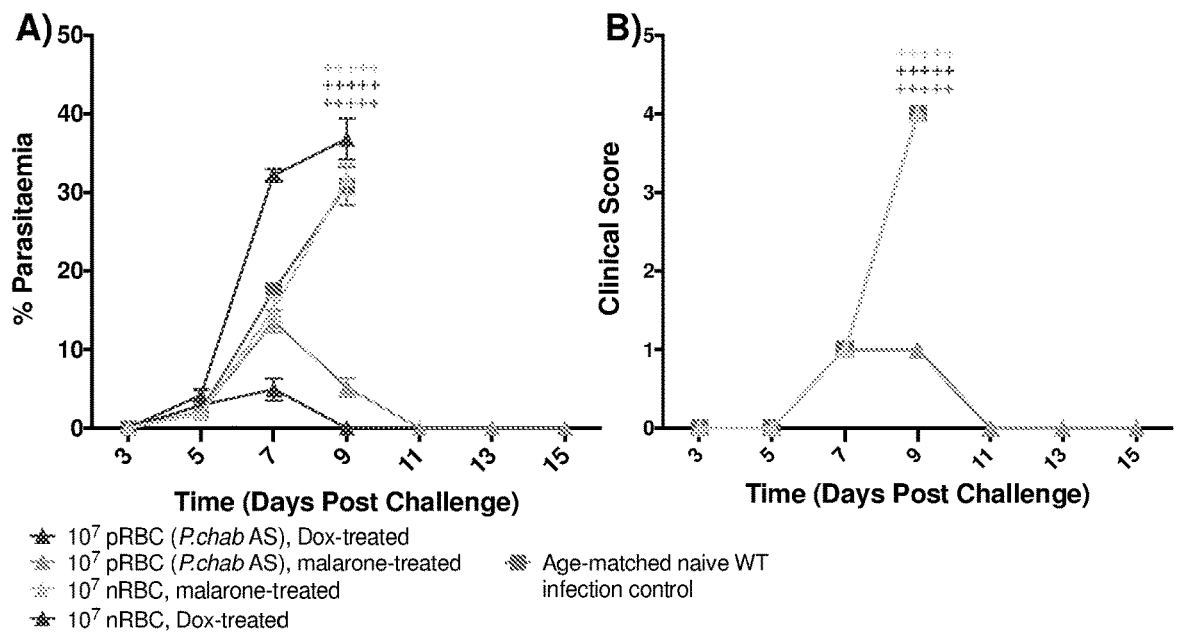
FIG. 7: Homologous challenge with $10^5$ *P. chabaudi* AS of C57BL6 mice receiving single infection with $10^7$ *P. chabaudi* AS and treated with doxycycline (intraperitoneal injection for 7 days) or malarone (orally for 4 days).

Reference is also made to FIG. 7, which provides initial data piloting the comparison of doxycycline vs malarone.

Figure 8:
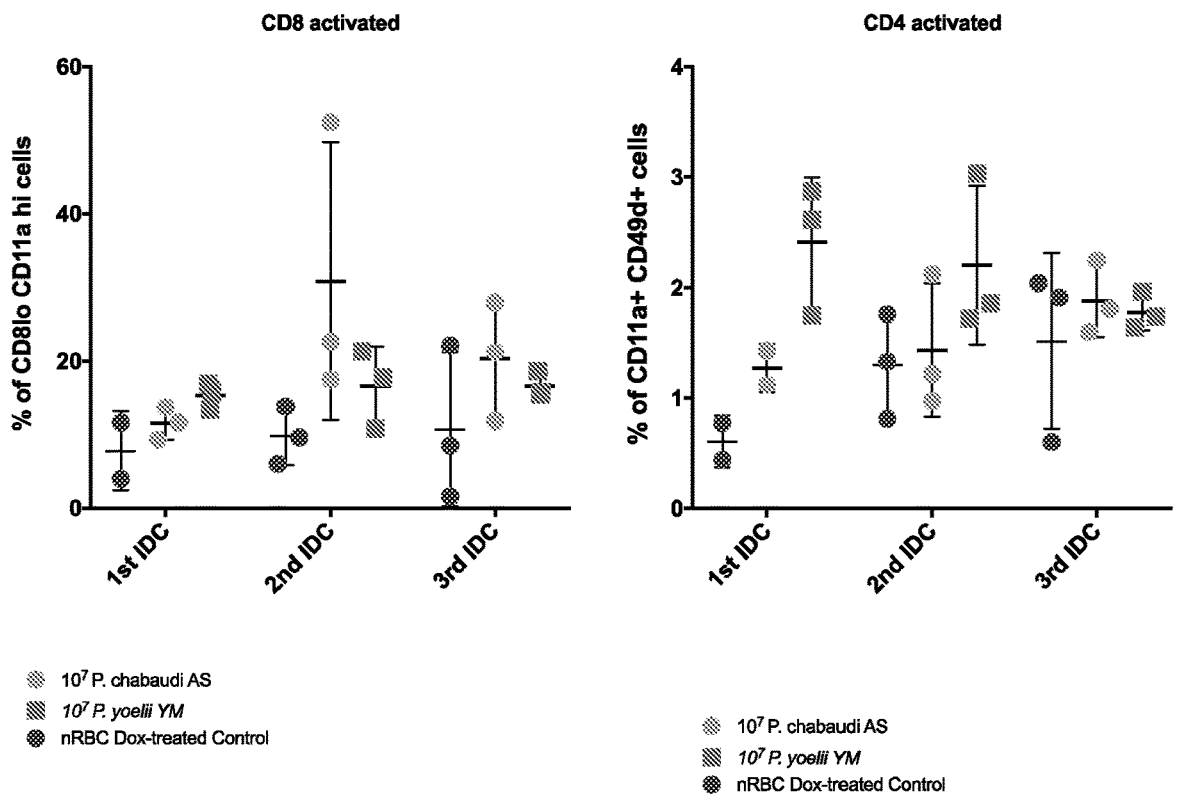
FIG. 8: Preliminary experiments investigating T-cell activation on Day 7 from day of infection after each IDC with $10^7$ *P. chabaudi* AS or $10^7$ *P. yoelii* YM.
Figure 9:
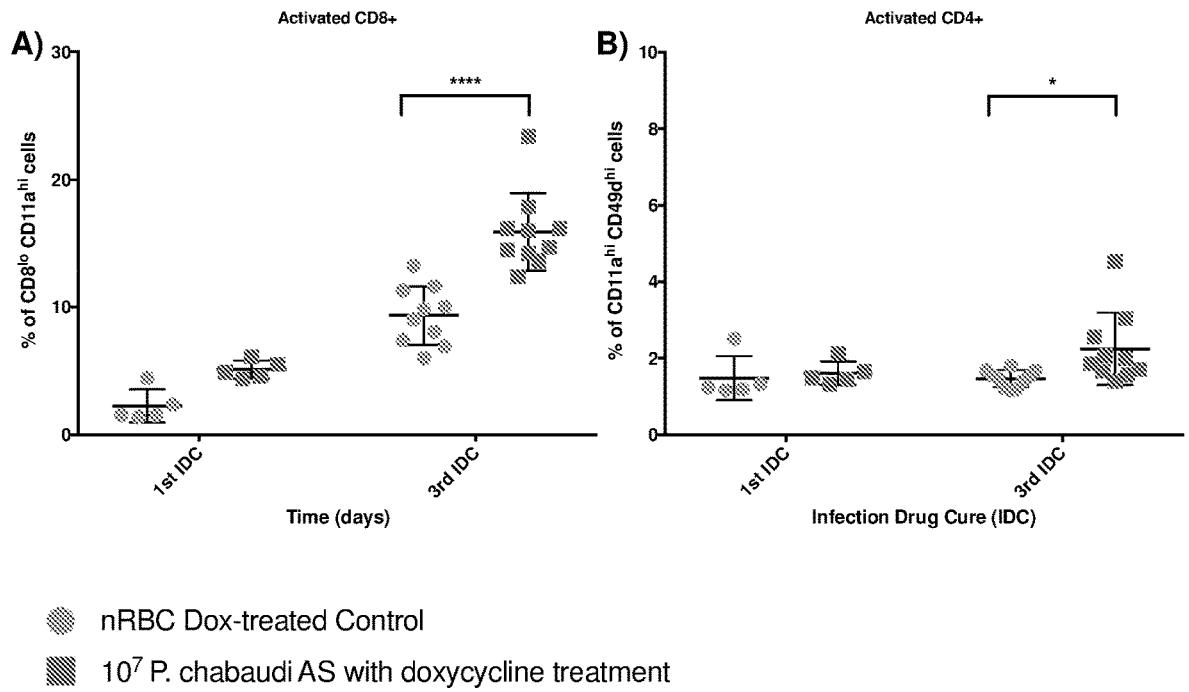
FIG. 9: T-cell activation after the $1^{st}$ (n=5/group) and $3^{rd}$ IDC (n=10/group) with *P. chabaudi* AS in BALB/c mice. Peripheral blood from mice was collected on Day 7 post infection with *P. chabaudi* AS (or 1 day after the completion of the IDC regime) and used to identify activated circulating CD4+ and CD8+ T-cells following IDC. Activated CD8+ T cells (A) were identified as expressing $CD8^{lo}CD11a^{hi}$ and activated CD4+(B) were identified as expressing $CD49d^{hi}CD11a^{hi}$. * indicates p<0.05, **** p<0.0001.
Figure 10:
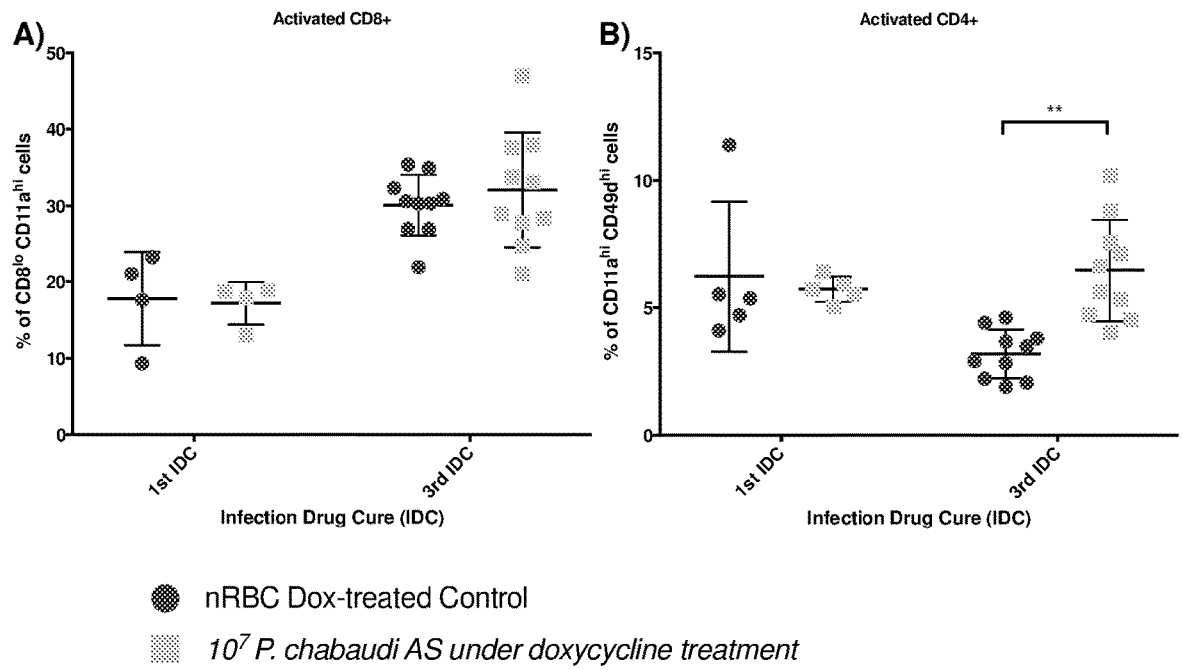
FIG. 10: T-cell activation after the $1^{st}$ and $3^{rd}$ IDC with *P. chabaudi* AS in C57/B6 mice (n=10/group). Peripheral blood from mice was collected on Day 7 post infection with *P. chabaudi* AS (or 1 day after the completion of the IDC regime) and used to identify activated circulating CD4+ and CD8+ T-cells following IDC. Activated CD8+ T cells (A) were identified as expressing $CD8^{lo}CD11a^{hi}$ and activated CD4+(B) were identified as expressing $CD49d^{hi}CD11a^{hi}$. ** indicates p<0.01.

FIG. 8 provides the results of preliminary experiments showing T-cell activation on Day 7 from day of infection after each IDC with *P. chabaudi* and *P. yoelii*. Further investigation in BALB/c and C57/B6 mice has shown that CD8 and CD4 activation is increased after three cycles of infection/drug cure (FIGS. 9 and 10).

Figure 11:
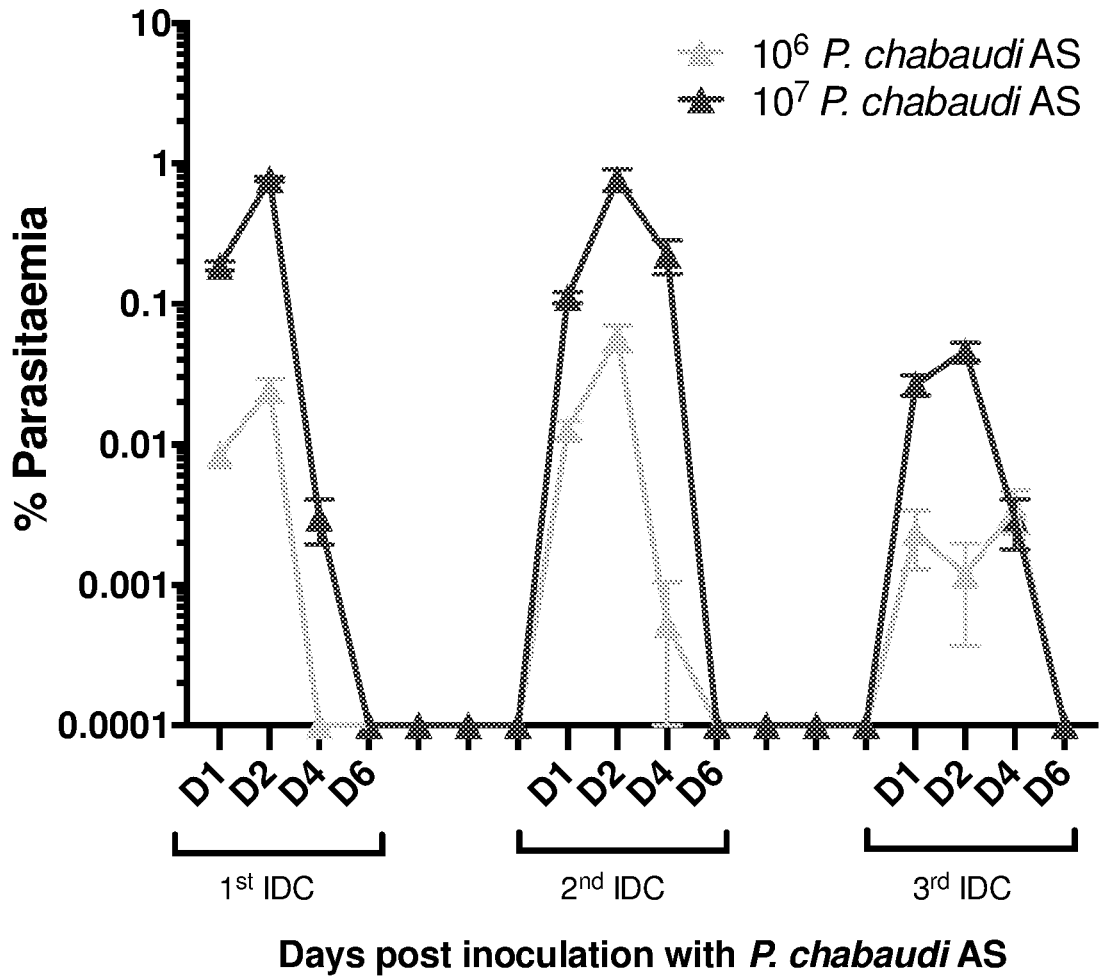
FIG. 11: Parasitaemia, as determined by counting number of parasites in 20 fields, in BALB/c mice that received three doses of $10^6$ or $10^7$ *P. chabaudi* AS trophozoite parasites under doxycycline treatment (50 mg/kg). Results are the mean±SEM of 2 independent experiments.
Figure 12:
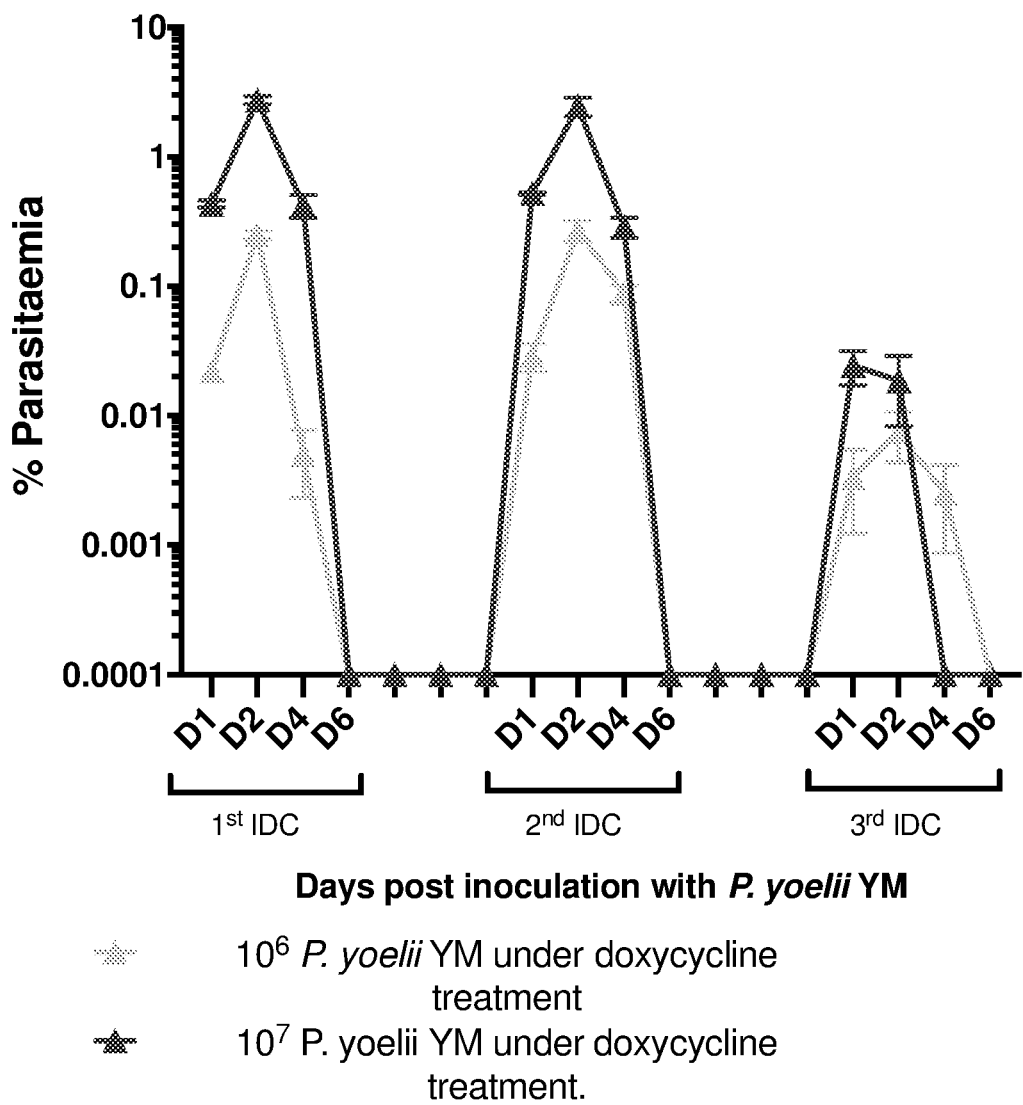
FIG. 12: Parasitaemia, as determined by counting number of parasites in 20 fields, in BALB/c mice that received three doses of $10^6$ or $10^7$ *P. yoelii* YM trophozoite parasites under doxycycline treatment (50 mg/kg).

FIGS. 11 and 12 demonstrates persistence of parasites as seen in blood films during infection/drug cure with *P. chabaudi* or *P. yoelii* in BALB/c mice. These data show mice (n=10) receiving either $10^6$ or $10^7$ *P. chabaudi* (FIG. 11) or *P. yoelii* (FIG. 12) blood stage parasites over a course of infection/drug cure. Blood smears were performed on D1, 2, 4 and 6 post infection during IDC 1, 2 and 3.

Further experiments will involve investigation of protection from heterologous challenge in BALB/c and C57/B6 mice receiving 3×IDC with *P. chabaudi* or *P. yoelii*, as well as associated immunology. Additionally, we are also investigating the use of a gel to allow the slow release of doxycycline into the circulation to reduce the treatment period.

We have also started human experiments. Initially we have given two volunteers a blood stage infection initiated with 3×$10^6$ magnet-purified *P. falciparum* trophozoite-parasitized human red cells (pRBC). At the same time, volunteers were administered 100 mg doxycycline once daily for 21 days, although this could be changed to twice daily. A controlled release form of doxycycline (such as Atridox® comprising doxycycline hyclate) will also be tested. Parasitemia was monitored by pPCR using the conditions, primers and probes shown in Tables 1 and 2.

Parasite concentration is determined whereby the $\log_{10}$ of each known concentration of a standard concentration range is plotted against the quantification cycle of Cq values of the test samples in a linear regression model (y=mx+b) using Biorad CFX manager 2.1 software.

Figure 13:
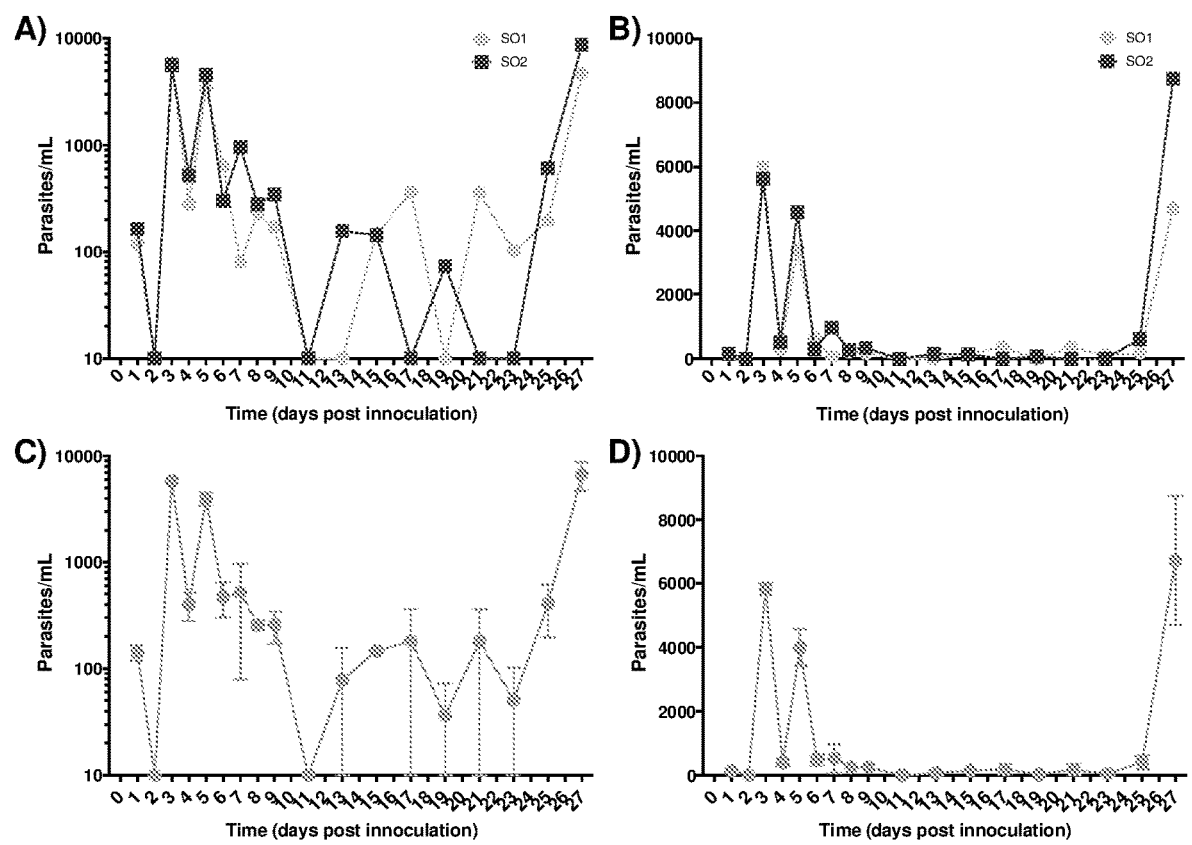
FIG. 13: Persistence of *P. falciparum* 7G8 in volunteers receiving doxycycline chemoprophylaxis. Top panel shows parasitaemia, as determined by qPCR, in individual volunteers on A) logarithmic or B) linear scale. Bottom panel shows the mean parasitaemia on a C) logarithmic and D) linear scale. Volunteers received 3×106 pRBCs on D0, followed by doxycycline treatment administered orally (100 mg/day) from D0 to D20.

The human volunteers did not become ill and almost cleared their infection after 23 days (FIG. 13). Subsequently, it has been found that malaria parasite growth was suppressed in the volunteers up to day 25. Following cessation of treatment with doxycycline, exponential growth of the malaria parasites was observed in the volunteers indicating an active malaria infection. Riamet treatment was initiated on day 28.

The efficacy of this delayed death vaccine approach will also be tested using Babesia *microti* parasites and a delayed death agent in a rodent model of babesiosis.

Throughout the specification, the aim has been to describe the preferred embodiments of the invention without limiting the invention to any one embodiment or specific collection of features. Various changes and modifications may be made to the embodiments described and illustrated without departing from the present invention.

The disclosure of each patent and scientific document, computer program and algorithm referred to in this specification is incorporated by reference in its entirety.

TABLE 1

| PCR conditions | | | |
|---|---|---|---|
| | Temperature | Time | # of Cycles |
| Preincubation | 95° C. | 15 min | 1 |
| Denaturation | 95° C. | 15 seconds | 45 |
| Annealing/extension | 60° C. | 60 seconds | |

TABLE 2

| Primers and probes | | | |
|---|---|---|---|
| Name | Sequence | Supplier | Ref |
| Primer 18SPFR-F | 5'-CTTTTGAGAGGTTTTGTTACTTTGAGTAA-3' (SEQ ID NO: 1) | SIGMA | 1 |
| Primer 18SPFR-R | 5'-TATTCCATGCTGTAGTATTCAAACACA-3' (SEQ ID NO: 2) | SIGMA | 1 |
| Taqman probe 18SPFR-F | FAM-5'-TGTTCATAACAGACGGGTAGTCATGATTGAGTTCA-3'-BHQ1 (SEQ ID NO: 3) | Biosearch Technologies | 1 |
| Primer EQHSV-330F | 5'-GATGACACTAGCGACTTCGA-3' (SEQ ID NO: 4) | SIGMA | 2 |
| Primer EQHSV-410R | 5'-CAGGGCAGAAACCATAGACA-3' (SEQ ID NO: 5) | SIGMA | 2 |
| Taqman probe EquHSV-360 | FAM-5'-TTTCGCGTGCCTCCTCCAG-3'-BHQ1 (SEQ ID NO: 6) | Biosearch Technologies | 1 |

1. Rebecca J Rockett et al., Malaria Journal 2011, 10:48.
2. S Bialasiewicz et al., Sex Transm infect 2009 85:102-105.

REFERENCES

Bialasiewicz, S., *Sex Trans. Infect.* 85:102, 2009
Draper, M. P. et al., *Antimicrobial Agents & Chemotherapy* 57: 3131, 2013
Elliott, S., R. et al, *Infect. Immun.* 73:2478, 2005
McCarthy, J. and Good, M. F. *Hum. Vaccine* 6:114, 2010
Makobongo, M. et al., *Proc. Natl. Acad. Sci. USA* 100:2628, 2003
Pinzon-Charry, A. et al., *J. Clin. Invest.* 120:2967, 2010
Pombo, D. J. et al., *Lancet* 360:610, 2002
Rockett, R. J., *Malaria J.* 10:48, 2011

The invention claimed is:

1. A method of eliciting in an animal a protective immune response to an apicomplexan parasite selected from the group consisting of *Plasmodium* and Babesia, said method including the steps of:
   identifying an animal requiring a protective immune response to the apicomplexan parasite; and
   co-administering within 48 hours to the animal blood-stage apicomplexan parasites or red blood cells infected with said apicomplexan parasites (pRBC) via injection, and a delayed death agent selected from the group consisting of a tetracycline antibiotic and macrolide antibiotic to thereby produce a controlled avirulent infection that elicits a protective immune response to the apicomplexan parasite in said animal, wherein said animal is selected from the group consisting of a human, bovine, and canine.

2. A method of immunizing an animal against an apicomplexan parasite infection, said method including the steps of:
   identifying an animal requiring a protective immune response to an apicomplexan parasite selected from the group consisting of *Plasmodium* and Babesia; and co-administering within 48 hours to the animal blood-stage apicomplexan parasites or red blood cells infected with said apicomplexan parasites (pRBC) via injection, and a delayed death agent selected from the group consisting of a tetracycline antibiotic and macrolide antibiotic to thereby produce a controlled avirulent infection that elicits an immune response, to thereby immunize the animal against the apicomplexan parasite infection, wherein said animal is selected from the group consisting of a human, bovine, and canine.

3. The method of claim 1, which does not include the step of administering an adjuvant.

4. The method of claim 2, which does not include the step of administering an adjuvant.

5. The method of claim 1, wherein the delayed death agent is in a slow, controlled, or delayed release formulation.

6. The method of claim 2, wherein the delayed death agent is in a slow, controlled, or delayed release formulation.

7. The method of claim 1, wherein the apicomplexan parasites or red blood cells infected with said apicomplexan parasites and the delayed death agent are administered to the animal in a temporal window whereby the delayed death agent can allow no more than one, two, three, four or five cycles of replication by the apicomplexan parasites before killing the apicomplexan parasites.

8. The method of claim 7, wherein the delayed death agent is initially administered before, together with, or no more than 0.5 to 12 hours after, administration of the blood stage apicomplexan parasites or pRBC.

9. The method of claim 1, wherein after an initial administration of the blood stage apicomplexan parasites or pRBC and delayed death agent, one or a plurality of further doses of the blood stage apicomplexan parasites, pRBC and/or delayed death agent are administered to the animal.

10. The method of claim 2, wherein the apicomplexan parasites or red blood cells infected with said apicomplexan parasites and the delayed death agent are administered to the animal in a temporal window whereby the delayed death agent can allow no more than one, two, three, four or five cycles of replication by the apicomplexan parasites before killing the apicomplexan parasites.

11. The method of claim 10, wherein the delayed death agent is initially administered before, together with, or no more than 0.5 to 12 hours after, administration of the blood stage apicomplexan parasites or pRBC.

12. The method of claim 2, wherein after an initial administration of the blood stage apicomplexan parasites or pRBC and delayed death agent, one or a plurality of further doses of the blood stage apicomplexan parasites, pRBC and/or delayed death agent are administered to the animal.

13. A method of eliciting in a bovine a protective immune response to Babesia, said method including the steps of:
identifying a bovine requiring a protective immune response to Babesia; and
co-administering within 48 hours to the bovine blood-stage Babesia or red blood cells infected with Babesia (pRBC) via injection and a delayed death agent to the bovine to thereby produce a controlled avirulent infection that elicits a protective immune response to Babesia in said bovine, wherein the delayed death agent is in a slow, controlled or delayed release formulation and is selected from the group consisting of a tetracycline antibiotic and macrolide antibiotic.

14. A method of immunizing a bovine against a Babesial parasite infection, said method including the steps of:
identifying a bovine requiring immunization against Babesia; and
co-administering within 48 hours to the bovine blood-stage Babesia or red blood cells infected with Babesia (pRBC) via injection and a delayed death agent to the bovine to thereby produce a controlled avirulent infection that elicits an immune response, to thereby immunize the bovine against the Babesial infection, wherein the delayed death agent is in a slow, controlled or delayed release formulation, and is selected from the group consisting of a tetracycline antibiotic and macrolide antibiotic.

15. A method of eliciting in a bovine a protective immune response to Babesia, said method including the steps of:
identifying a bovine requiring a protective immune response to Babesia; and
co-administering within 48 hours to the bovine blood-stage Babesia or red blood cells infected with Babesia (pRBC) via injection and a delayed death agent to the bovine to thereby produce a controlled avirulent infection that elicits a protective immune response to the Babesia in said bovine, wherein after an initial administration of the blood stage Babesia or pRBC and delayed death agent, one or a plurality of further doses of blood stage Babesia, pRBC and/or delayed death agent are administered to the bovine, wherein the delayed death agent is selected from the group consisting of a tetracycline antibiotic and macrolide antibiotic.

16. A method of immunizing a bovine against a Babesial parasite infection, said method including the steps of:
identifying a bovine requiring a protective immune response to Babesia; and
co-administering within 48 hours to the bovine blood-stage Babesia or red blood cells infected with Babesia (pRBC) via injection and a delayed death agent selected from the group consisting of a tetracycline antibiotic and macrolide antibiotic to the bovine to thereby produce a controlled avirulent infection that elicits an immune response, to thereby immunize the bovine against the Babesial parasite infection, wherein after an initial administration of the blood stage Babesia or pRBC and delayed death agent, one or a plurality of further doses of blood stage Babesia, pRBC and/or delayed death agent are administered to the bovine.

17. The method of claim 13, wherein the delayed death agent is initially administered before, together with, or no more than 0.5 to 12 hours after, administration of the blood stage Babesia or pRBC.

18. The method of claim 14, wherein the delayed death agent is initially administered before, together with, or no more than 0.5 to 12 hours after, administration of the blood stage Babesia or pRBC.

19. The method of claim 15, wherein the delayed death agent is initially administered before, together with, or no more than 0.5 to 12 hours after, administration of the blood stage Babesia or pRBC.

20. The method of claim 16, wherein the delayed death agent is initially administered before, together with, or no more than 0.5 to 12 hours after, administration of the blood stage Babesia or pRBC.

* * * * *

SEQUENCE LISTING

```
<160> NUMBER OF SEQ ID NOS: 6

<210> SEQ ID NO 1
<211> LENGTH: 29
<212> TYPE: DNA
<213> ORGANISM: Artificial Sequence
<220> FEATURE:
<223> OTHER INFORMATION: Synthetic primer
```

```
<400> SEQUENCE: 1
cttttgagag gttttgttac tttgagtaa                                              29

<210> SEQ ID NO 2
<211> LENGTH: 27
<212> TYPE: DNA
<213> ORGANISM: Artificial Sequence
<220> FEATURE:
<223> OTHER INFORMATION: Synthetic primer

<400> SEQUENCE: 2
tattccatgc tgtagtattc aaacaca                                                27

<210> SEQ ID NO 3
<211> LENGTH: 35
<212> TYPE: DNA
<213> ORGANISM: Artificial Sequence
<220> FEATURE:
<223> OTHER INFORMATION: Synthetic primer

<400> SEQUENCE: 3
tgttcataac agacgggtag tcatgattga gttca                                       35

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
gatgacacta gcgacttcga                                                        20

<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5
cagggcagaa accatagaca                                                        20

<210> SEQ ID NO 6
<211> LENGTH: 19
<212> TYPE: DNA
<213> ORGANISM: Artificial Sequence
<220> FEATURE:
<223> OTHER INFORMATION: Synthetic primer

<400> SEQUENCE: 6
tttcgcgtgc ctcctccag                                                         19
```